US012716055B2

(12) United States Patent
O'Heeron et al.

(10) Patent No.: US 12,716,055 B2
(45) Date of Patent: Aug. 25, 2026

(54) TREATMENT OF DISC DEGENERATIVE DISEASE AND STIMULATION OF PROTEOGLYCAN SYNTHESIS BY FIBROBLAST CONDITIONED MEDIA AND FORMULATIONS THEREOF

(71) Applicant: FIBROBIOLOGICS, INC., Houston, TX (US)

(72) Inventors: Pete O'Heeron, Houston, TX (US); Thomas Ichim, San Diego, CA (US)

(73) Assignee: Fibrobiologics, Inc., Houston, TX (US)

(*) Notice: Subject to any disclaimer, the term of this patent is extended or adjusted under 35 U.S.C. 154(b) by 492 days.

(21) Appl. No.: 18/321,121

(22) Filed: May 22, 2023

(65) Prior Publication Data

US 2023/0407258 A1 Dec. 21, 2023

Related U.S. Application Data

(63) Continuation of application No. 17/022,897, filed on Sep. 16, 2020, now Pat. No. 11,732,239.

(60) Provisional application No. 62/901,164, filed on Sep. 16, 2019.

(51) Int. Cl.

| | |
|---|---|
| ***C12N 5/07*** | (2010.01) |
| ***A61K 9/00*** | (2006.01) |
| ***A61K 35/15*** | (2025.01) |
| ***A61K 35/33*** | (2015.01) |
| ***C12N 5/077*** | (2010.01) |
| ***C12N 5/0784*** | (2010.01) |

(52) U.S. Cl.

CPC ............ *C12N 5/0656* (2013.01); *A61K 35/15* (2013.01); *A61K 35/33* (2013.01); *C12N 5/0639* (2013.01); *A61K 9/0019* (2013.01); *A61K 9/0053* (2013.01); *C12N 2501/10* (2013.01); *C12N 2501/599* (2013.01)

(58) Field of Classification Search

CPC ........................... C12N 5/0656; C12N 5/0639; C12N 2501/10; C12N 2501/599; C12N 2501/05; C12N 2501/052; C12N 2501/056; C12N 2501/999; A61K 35/15; A61K 35/33; A61K 9/0019; A61K 9/0053; A61K 31/485; A61K 35/28; A61P 19/02

See application file for complete search history.

(56) References Cited

U.S. PATENT DOCUMENTS

| | | | |
|---|---|---|---|
| 4,857,533 | A | 8/1989 | Sherman et al. |
| 6,156,312 | A | 12/2000 | Leskovar |
| 2004/0101959 | A1 | 5/2004 | Marko et al. |
| 2006/0193857 | A1 | 8/2006 | Boruchov et al. |
| 2008/0038199 | A1 | 2/2008 | Hong et al. |
| 2019/0249144 | A1 | 8/2019 | Hermatti et al. |

FOREIGN PATENT DOCUMENTS

| | | |
|---|---|---|
| WO | WO 1992/006708 | 4/1992 |
| WO | WO 2018/132594 | 7/2018 |
| WO | WO 2018/195308 | 10/2018 |
| WO | WO 2019/124500 B5 | 6/2019 |
| WO | WO 2019/213518 | 11/2019 |

OTHER PUBLICATIONS

Â¢ Chee et al., (2016) Cell therapy with human dermal fibroblasts enhances intervertebral disk repair and decreases inflammation in the rabbit model. Global Spine Journal, 6(8): pp. 771-779 (Year: 2016).*

Â¢ Shi et al., (2019) Therapeutic effects of cell therapy with neonatal human dermal fibroblasts and rabbit dermal fibroblasts on disc degeneration and inflammation. The Spine Journal, 19(1): pp. 171-181 (Year: 2019).*

Regan et al. "Regulation and functional implications of opioid receptor splicing in opioid pharmacology and HIV pathogenesis", *Journal of Cellular Physiology,* vol. 231, No. 5, pp. 976-985, 2015.

Cheng et al., "Mesenchymal stem cells deliver exogenous miR-21 via exosomes to inhibit nucleus pulposus cell apoptosis and reduce intervertebral disc degeneration," Journal of Cellular and Molecular Medicine, 22(1):261-276, 2018.

Extended European Search Report issued in European Patent Application No. 20866096.9, dated Jun. 19, 2023.

Immonen et al., "Selective blockade of the OGF-OGFr pathway by naltrexone accelerates fibroblast proliferation and wound healing," Experimental Biology and Medicine, 239(10):1300-1309, 2014.

Maerz et al., "Molecular and genetic advances in the regeneration of the intervertebral disc," Surgical Neurology International, 4(Suppl. 2):S94-S2015, 2013.

Marfia et al., "Potential use of human adipose mesenchymal stromal cells for intervertebral disc regeneration: a preliminary study on biglycan-deficient murine model of chronic disc degeneration," Arthritis Research & Therapy, 16(5):457, 13 pages, 2014.

Tamama et al., "Epidermal Growth Factor (EGF) Treatment on Multipotential Stromal Cells (MSCs). Possible Enhancement of Therapeutic Potential of MSC," Journal of Biomedicine and Biotechnology, 2010:795385, 11 pages, 2010.

Wei et al., "Mesenchymal stem cells: potential application in intervertebral disc regeneration," Transl. Pediatr., 3(2):71-90, 2014.

Azizi et al. "A Survey on the Adjuvant Role of Natoxone Alone or Combined with Alum in Vaccination Against Fasclolosls in BALB/c Mice," Acta Parasltologica, Feb. 20, 2019 (Feb. 20, 2019), vol. 64, pp. 236-245.

(Continued)

*Primary Examiner* — Kara D Johnson

(74) *Attorney, Agent, or Firm* — Norton Rose Fulbright US LLP

(57) ABSTRACT

In some aspects, disclosed are methods and compositions for disc regeneration and/or repair using one or more components from conditioned media from fibroblasts. In certain cases, conditioned media is obtained from fibroblasts stimulated with one or more opioid receptor antagonists and one or more toll-like receptor agonists. Conditioned media from fibroblasts may be provided in an effective amount to an individual in need thereof.

8 Claims, 1 Drawing Sheet

(56) References Cited

OTHER PUBLICATIONS

Ichim et al. "Fibroblasts as a Practical Alternative to Mesenchymal Stem Cells,". Journal of Translational Medicine, Jul. 27, 2018 (Jul. 27, 2018), vol. 16, No. 212, pp. 1-9.
Lu et al., "Mesenchymal stem cell-derived exosomes as a novel strategy for the treatment of intervertebral disc degeneration," vol. 9 (Jan. 24, 2022) Article 770510 (Year: 2022).
Sayed et al. "Transdifferentlation of Human Fibroblasts to Endothelial Cells." Circulation, Jan. 20, 2015 (Jan. 20, 2015), vol. 131, Iss. 3, pp. 300-309.
Zheng et al., "Effect of conditioned medium from human umbilical cord-derived mesenchymal stromal cells on rejuvenation of nucleus pulposus derived stem/progenitor cells from degenerated intervertebral disc," International Journal of Stem Cells, vol. 13, No. 2 (2020) pp. 257-267 (Year 2020).

* cited by examiner

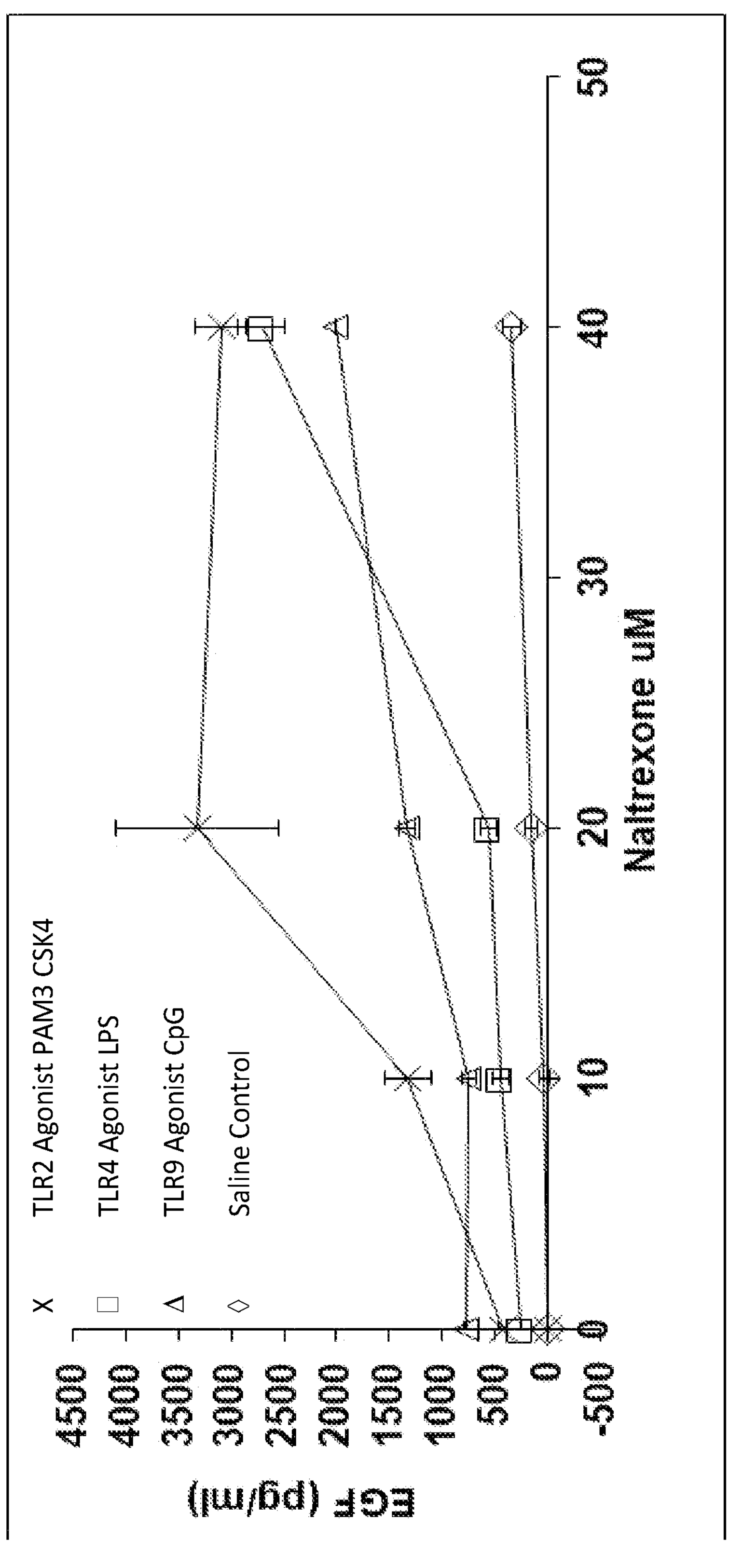
TLR2 Agonist PAM3 CSK4
TLR4 Agonist LPS
TLR9 Agonist CpG
Saline Control
EGF (pg/ml)
4500
4000
3500
3000
2500
2000
1500
1000
500
0
-500
0
10
20
30
40
50
Naltrexone uM

TREATMENT OF DISC DEGENERATIVE DISEASE AND STIMULATION OF PROTEOGLYCAN SYNTHESIS BY FIBROBLAST CONDITIONED MEDIA AND FORMULATIONS THEREOF

This application is a continuation of U.S. patent application Ser. No. 17/022,897, filed Sep. 16, 2020, which claims priority to U.S. Provisional Patent Application Ser. No. 62/901,164, filed Sep. 16, 2019, which are each incorporated by reference herein in their entirety.

TECHNICAL FIELD

Embodiments of the disclosure include at least the fields of cell biology, molecular biology, and medicine.

BACKGROUND

Intervertebral discs are made of highly organized matrices of collagen, water, and proteoglycans. Proteoglycan production in the discs is believed to occur by differentiated chondrocytes. Each intervertebral disc comprises a central highly hydrated and gelatinous nucleus pulposus (nucleus) surrounded by an elastic and highly fibrous annulus fibrosus (annulus). Cartilaginous endplates provide a connection to the vertebrae inferiorly and superiorly to the intervertebral disc. This cushioned arrangement within the intervertebral discs allows the discs to facilitate movement and flexibility within the spine while dissipating hydraulic pressure through the spine.

During aging, mechanical stress, and/or as a result of other environment and/or genetic changes, the intervertebral disc may begin to degenerate. It is known that with aging, the matrix of the disc undergoes substantial structural, molecular, and mechanical changes. The present disclosure satisfies a long felt need in the art of compositions and methods for treatment of disc degeneration.

BRIEF SUMMARY

This disclosure is directed to methods and compositions related to promoting disc regeneration and/or repair in an individual. Disclosed herein are methods for promoting disc regeneration and/or repair in an individual using one or more components from stimulated fibroblasts. In particular embodiments, compositions of the present disclosure comprise one or more components from fibroblasts cultured with one or more opioid receptor antagonists and one or more toll-like receptor (TLR) agonists. Some embodiments pertain to isolation of fibroblast regenerative cells from a population of cells and, optionally, using components in the media in which the cultured fibroblasts for a therapeutic purpose.

In some embodiments, provided herein is a composition comprising one or more components derived from fibroblast cells cultured with one or more opioid receptor antagonists and one or more TLR agonists. The one or more components may be derived from media from the culture of the fibroblast cells. The one or more components may comprise one or more growth factors, for example, epidermal growth factor (EGF), vascular endothelial growth factor (VEGF), fibroblast growth factor (FGF)-1, FGF-2, FGF-5, FGF-15, insulin like growth factor (IGF), placental growth factor, and hepatocyte growth factor (HGF), and in particular embodiments the one or more growth factors derive from fibroblasts that have been cultured under particular conditions. In some embodiments, the one or more components comprise exosomes. The exosomes may comprise one or more markers, for example, CD9. In some embodiments, the exosome is capable of binding to a dendritic cell and/or a mesenchymal stem cell. In further aspects, the one or more components were derived from fibroblast cells cultured with one or more opioid receptor antagonists and one or more TLR agonists in a proliferative state for the cells.

In some embodiments, the opioid receptor antagonist is naltrexone, 6B-naltrexol, nalmefene, naloxone, N-methylnaltrexone, alvimopan, diprenorphine, nalorphine, nalorphine dinicotinate, levallorphan, samidorphan, nalodeine, naloxegol, axelopran, bevenopran, methylsamidorphan, naldemedine, or a combination thereof. In some embodiments, the TLR agonist is Pam3CSK4, LPS, CpG DNA, Poly (ic), flagellin, MALP-2, imiquimod, resmiquimod, zymosan, or a combination thereof. In some embodiments, the fibroblast cell expresses a marker selected from the group consisting of Oct-4, Nanog, Sox-2, KLF4, c-Myc, Rex-1, GDF-3, LIF receptor, CD105, CD117, CD344, Stella, and a combination thereof. In further embodiments, the fibroblast cell expresses a marker selected from the group consisting of CD10, CD13, CD44, CD73, CD90, CD141, PDGFr-alpha, HLA-A, HLA-B, HLA-C, and a combination thereof. In some cases, the fibroblast cell does not express a marker from the group consisting of MHC class I, MHC class II, CD45, CD13, CD49c, CD66b, CD73, CD105, CD90, and a combination thereof. In some cases, the fibroblast cell does not express a marker selected from the group consisting of CD31, CD34, CD45, CD117, CD141, HLA-DR, HLA-DP, HLA-DQ, and a combination thereof.

In further aspects, provided is a method of promoting disc regeneration in an individual, the method comprising providing to the individual an effective amount of one or more components derived from fibroblast cells cultured with one or more opioid receptor antagonists and one or more toll-like receptor (TLR) agonists. In some cases, a method for promoting disc regeneration comprises providing to the individual an effective amount of fibroblast cells (and/or components derived therefrom) previously cultured with one or more opioid receptor antagonists and one or more TLR agonists. Fibroblast cells cultured with one or more opioid receptor antagonists and one or more TLR agonists, and/or one or more components (e.g., one or more regenerative factors) therefrom, may be provided to an individual in any suitable delivery route, including at least locally (such as intradiscally) or systemically.

In some embodiments, provided herein is a method for improving efficacy of a tolerogenic therapy, the method comprising (a) providing the tolerogenic therapy to an individual and (b) providing to the individual an amount of one or more opioid receptor antagonists sufficient to enhance the efficacy of the tolerogenic therapy. The tolerogenic therapy may comprise autoantigen administration, which may be administered intravenously and/or orally. In some embodiments, the autoantigen administration comprises providing immature antigen presenting cells comprising the autoantigen, providing tolerogenic antigen presenting cells comprising the autoantigen, providing mesenchymal stem cells comprising the autoantigen, providing hematopoietic stem cells comprising the autoantigen, and/or providing allogenic mesenchymal stem cells. The tolerogenic antigen presenting cells may be dendritic cells, in some cases.

BRIEF DESCRIPTION OF THE DRAWINGS

FIG. 1 shows epidermal growth factor (EGF) production from neonatal foreskin cells cultured with naltrexone and the indicated toll-like receptor (TLR) agonists.

DETAILED DESCRIPTION

I. Examples of Definitions

In keeping with long-standing patent law convention, the words "a" and "an" when used in the present specification in concert with the word comprising, including the claims, denote "one or more." As used in the specification and claims, the singular form "a", "an", and "the" include plural references unless the context clearly dictates otherwise. For example, the term "a nucleic acid" includes a plurality of nucleic acids, including mixtures thereof. Some embodiments of the disclosure may consist of or consist essentially of one or more elements, method steps, and/or methods of the disclosure. It is contemplated that any method or composition described herein can be implemented with respect to any other method or composition described herein and that different embodiments may be combined.

As used herein, the term "about" or "approximately" refers to a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length. In particular embodiments, the terms "about" or "approximately" when preceding a numerical value indicates the value plus or minus a range of 15%, 10%, 5%, or 1%. With respect to biological systems or processes, the term can mean within an order of magnitude, preferably within 5-fold, and more preferably within 2-fold, of a value. Unless otherwise stated, the term 'about' means within an acceptable error range for the particular value.

The term "administered" or "administering", as used herein, refers to any method of providing a composition to an individual such that the composition has its intended effect on the patient. For example, one method of administering is by an indirect mechanism using a medical device such as, but not limited to a catheter, applicator gun, syringe etc. A second exemplary method of administering is by a direct mechanism such as, local tissue administration, oral ingestion, transdermal patch, topical, inhalation, suppository etc.

As used herein, "allogeneic" refers to tissues or cells or other material from another body that in a natural setting are immunologically incompatible or capable of being immunologically incompatible, although from one or more individuals of the same species.

As used herein, the term "allotransplantation" refers to the transplantation of organs, tissues, and/or cells from a donor to a recipient, where the donor and recipient are different individuals, but of the same species. Tissue transplanted by such procedures is referred to as an allograft or allotransplant.

As used herein, the terms "allostimulatory" and "alloreactive" refer to stimulation and reaction of the immune system in response to an allologous antigens, or "alloantigens" or cells expressing a dissimilar HLA haplotype.

As used herein, "autologous" refers to tissues or cells or other material that are derived or transferred from the same individual's body (i.e., autologous blood donation; an autologous bone marrow transplant).

As used herein, the term "autotransplantation" refers to the transplantation of organs, tissues, and/or cells from one part of the body in an individual to another part in the same individual, i.e., the donor and recipient are the same individual. Tissue transplanted by such "autologous" procedures is referred to as an autograft or autotransplant.

The term "biologically active" refers to any molecule having structural, regulatory or biochemical functions. For example, biological activity may be determined, for example, by restoration of wild-type growth in cells lacking protein activity. Cells lacking protein activity may be produced by many methods (i.e., for example, point mutation and frame-shift mutation). Complementation is achieved by transfecting cells that lack protein activity with an expression vector that expresses the protein, a derivative thereof, or a portion thereof. In other cases, a fragment of a gene product (such as a protein) may be considered biologically active (or it may be referred to as functionally active) if it retains the activity of the full-length gene product, although it may be at a reduced but detectable level of the activity of the full-length gene product.

"Cell culture" is an artificial in vitro system containing viable cells, whether quiescent, senescent or (actively) dividing. In a cell culture, cells are grown and maintained at an appropriate temperature, typically a temperature of 37° C. and under an atmosphere typically containing oxygen and $CO_2$, although in other cases these are altered. Culture conditions may vary widely for each cell type though, and variation of conditions for a particular cell type can result in different phenotypes being expressed. The most commonly varied factor in culture systems is the growth medium. Growth media can vary in concentration of nutrients, growth factors, and the presence of other components. The growth factors used to supplement media are often derived from animal blood, such as calf serum.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

The term "drug", "agent" or "compound" as used herein, refers to any pharmacologically active substance capable of being administered that achieves a desired effect. Drugs or compounds can be synthetic or naturally occurring, non-peptide, proteins or peptides, oligonucleotides, or nucleotides (DNA and/or RNA), polysaccharides or sugars.

The term "individual", as used herein, refers to a human or animal that may or may not be housed in a medical facility and may be treated as an outpatient of a medical facility. The individual may be receiving one or more medical compositions via the internet. An individual may comprise any age of a human or non-human animal and therefore includes both adult and juveniles (i.e., children) and infants. It is not intended that the term "individual" connote a need for medical treatment, therefore, an individual may voluntarily or involuntarily be part of experimentation whether clinical or in support of basic science studies. The term "subject" or "individual" refers to any organism or animal subject that is an object of a method or material, including mammals, e.g., humans, laboratory animals (e.g., primates, rats, mice, rabbits), livestock (e.g., cows, sheep, goats, pigs, turkeys, and chickens), household pets (e.g., dogs, cats, and rodents), horses, and transgenic non-human animals.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the terms "or" and "and/or" are utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z." It is specifically contemplated that x, y, or z may be specifically excluded from an embodiment.

The term "pharmaceutically" or "pharmacologically acceptable", as used herein, refer to molecular entities and compositions that do not produce adverse, allergic, or other untoward reactions when administered to an animal or a human.

The term, "pharmaceutically acceptable carrier", as used herein, includes any and all solvents, or a dispersion medium including, but not limited to, water, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, and the like. Supplementary bioactive ingredients also can be incorporated into such carriers.

The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In one embodiment, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

"Therapeutic agent" means to have "therapeutic efficacy" in modulating angiogenesis and/or wound healing and an amount of the therapeutic is said to be a "angiogenic modulatory amount", if administration of that amount of the therapeutic is sufficient to cause a significant modulation (i.e., increase or decrease) in angiogenic activity when administered to a subject (e.g., an animal model or human patient) needing modulation of angiogenesis.

As used herein, the term "therapeutically effective amount" is synonymous with "effective amount", "therapeutically effective dose", and/or "effective dose" and refers to the amount of compound that will elicit the biological, cosmetic or clinical response being sought by the practitioner in an individual in need thereof. As one example, an effective amount is the amount sufficient to reduce immunogenicity of a group of cells. As a non-limiting example, an effective amount is an amount sufficient to promote formation of a blood supply sufficient to support the transplanted tissue. As another non-limiting example, an effective amount is an amount sufficient to promote formation of new blood vessels and associated vasculature (angiogenesis) and/or an amount sufficient to promote repair or remodeling of existing blood vessels and associated vasculature. The appropriate effective amount to be administered for a particular application of the disclosed methods can be determined by those skilled in the art, using the guidance provided herein. For example, an effective amount can be extrapolated from in vitro and in vivo assays as described in the present specification. One skilled in the art will recognize that the condition of the individual can be monitored throughout the course of therapy and that the effective amount of a compound or composition disclosed herein that is administered can be adjusted accordingly.

"Treatment," "treat," or "treating" means a method of reducing the effects of a disease or condition. Treatment can also refer to a method of reducing the disease or condition itself rather than just the symptoms. The treatment can be any reduction from pre-treatment levels and can be but is not limited to the complete ablation of the disease, condition, or the symptoms of the disease or condition. Therefore, in the disclosed methods, treatment" can refer to a 10%, 20%, 30%, 40%, 50%, 60%, 70%, 80%, 90%, or 100% reduction in the severity of an established disease or the disease progression, including reduction in the severity of at least one symptom of the disease. For example, a disclosed method for reducing the immunogenicity of cells is considered to be a treatment if there is a detectable reduction in the immunogenicity of cells when compared to pre-treatment levels in the same subject or control subjects. Thus, the reduction can be a 10, 20, 30, 40, 50, 60, 70, 80, 90, 100%, or any amount of reduction in between as compared to native or control levels. It is understood and herein contemplated that "treatment" does not necessarily refer to a cure of the disease or condition, but an improvement in the outlook of a disease or condition. In specific embodiments, treatment refers to the lessening in severity or extent of at least one symptom and may alternatively or in addition refer to a delay in the onset of at least one symptom.

II. Media from Stimulated Fibroblasts and Components Thereof

In some embodiments, the disclosure relates to components obtained from culture of fibroblast cells. Such components may be or may be obtained from cell culture media from fibroblasts cultured with one or more compounds that stimulate the production of regenerative factors from the fibroblasts. Components obtained from fibroblast cell culture may be useful in one or more of the methods disclosed herein including, for example, promoting disc regeneration or repair, treatment of a disc degenerative disease, and stimulation of proteoglycan synthesis.

In one embodiment, disclosed herein is the utilization of culture media or components present therein obtained from a tissue culture of fibroblasts. In specific embodiments, for use within the disclosed methods, fibroblast cells in the culture are in a proliferative state, said proliferative state being described as the cells not reaching confluency. In some embodiments, said fibroblast cells are growing in a 25%-75% confluent state. One or more components (e.g., regenerative factors) may be obtained from fibroblast cells growing in a proliferative state.

In some embodiments, utilization of an opioid receptor antagonist as a modulator of immune responses to self-antigens through stimulation of regulatory cell expansion by modification of fibroblast activity is disclosed. Stimulation of fibroblast production of regenerative factors may be accomplished through the treatment of fibroblasts with one or more opioid receptor antagonists. Examples of opioid receptor antagonists include, but are not limited to, naltrexone, 6B-naltrexol, nalmefene, naloxone, N-methylnaltrexone, alvimopan, diprenorphine, nalorphine, nalorphine dinicotinate, levallorphan, samidorphan, nalodeine, naloxegol, axelopran, bevenopran, methylsamidorphan, and/or naldemedine. Treatment of fibroblasts with an opioid receptor antagonist (e.g., naltrexone) is demonstrated herein to induce production of various growth factors including EGF. Additionally, upregulation of regenerative factor production is further disclosed by combination of opioid receptor antagonist (e.g., naltrexone) administration together with agonists of the toll like receptor (TLR) family such as the toll like receptor 2 agonist Pam3CSK4, the toll like receptor 4 agonist lipopolysaccharide (LPS), and the toll like receptor 9 agonist CpG. In some embodiments, a TLR-4 antagonist is used to stimulate fibroblasts instead of an opioid receptor antagonist. Example TLR-4 antagonists which may be used to stimulate fibroblasts include LPS and lipid A from *Rhodobacter sphaeroides*; LOS from *Bartonella quintana*; LPS from *Oscillatoria planktothrix* FP 1; curcumin from *Curcuma longa*, sulforaphane and iberin from cruciferous vegetables; xanthohumol from hops and beer, and celastrol from *Tripterygium wilfordii*.

TLRs can bind with damage-associated molecular patterns (DAMP) produced under stress or by tissue damage or cell apoptosis. It is believed that TLRs build a bridge between innate immunity and autoimmunity. There are five adaptors to TLRs including MyD88, TRIF, TIRAP/MAL, TRAM, and SARM. Upon activation, TLRs recruit specific adaptors to initiate the downstream signaling pathways leading to the production of inflammatory cytokines and chemokines. Under certain circumstances, ligation of TLRs drives to aberrant activation and unrestricted inflammatory responses, thereby contributing to the perpetuation of inflammation in autoimmune diseases. In the past, most studies focused on the intracellular TLRs, such as TLR3, TLR7, and TLR9, but recent studies reveal that cell surface TLRs, especially TLR2 and TLR4, also play an essential role in the development of autoimmune diseases and afford multiple therapeutic targets [Clin Rev Allergy Immunol. 47(2):136-47(2014)]. TLR4 is associated with hepatocytes and non-parenchymal cells, including Kupffer cells, myeloid dendritic cells, stellate cells, T-cells, NK cells, and sinusoidal endothelial cells. In recent years, some evidence suggests a likely mediating role of TLR-4 in the pathogenesis and progression of autoimmune liver diseases (AILDs) (He et al 2006; Longhi et al 2009; Mencin et al 2009). Monocytes from patients with PBC produce increased levels of proinflammatory cytokines such as IL-1.beta., IL-6, etc. when challenged with a variety of ligands, particularly those signaling through TLR4 and TLR5 (Mao et al 2005). Endogenous DAMPs are released subsequent to tissue damage. The ligands for TLR-2 and TLR-4 such as heat-shock proteins, HMGB1, hyaluronan, fibronectin, heparan sulfate and biglycan are produced to mediate sterile inflammation (Moreth et al 2014). The biological characteristics, signaling mechanisms of TLR2/4, the negative regulators of TLR2/4 pathway, and the pivotal function of TLR2/4 in the pathogenesis of autoimmune diseases including rheumatoid arthritis, systemic lupus erythematosus, systemic sclerosis, Sjogren's syndrome, psoriasis, multiple sclerosis, and autoimmune diabetes were recently reviewed by Liu Y, et al. [Clin Rev Allergy Immunol. 47(2):136-47(2014)].

Compositions of the present disclosure may be obtained from isolated fibroblast cells or a population thereof (including from a culture thereof) capable of proliferating and differentiating into ectoderm, mesoderm, or endoderm. In some embodiments, an isolated fibroblast cell expresses at least one of Oct-4, Nanog, Sox-2, KLF4, c-Myc, Rex-1, GDF-3, LIF receptor, CD105, CD117, CD344 or Stella markers. In some embodiments, an isolated fibroblast cell does not express at least one of MHC class I, MHC class II, CD45, CD13, CD49c, CD66b, CD73, CD105, or CD90 cell surface proteins. Such isolated fibroblast cells may be used as a source of conditioned media. The cells may be cultured alone, or may by cultured in the presence of other cells in order to further upregulate production of growth factors in the conditioned media.

Fibroblasts may be expanded and utilized by administration themselves, or may be cultured in a growth media in order to obtain conditioned media that may then be used (or that components thereof may be used). The term Growth Medium generally refers to a medium sufficient for the culturing of fibroblasts. In particular, one particular medium for the culturing of the cells of the disclosure herein comprises Dulbecco's Modified Essential Media (DMEM). IN particular embodiments it is DMEM-low glucose (also DMEM-LG herein) (Invitrogen, Carlsbad, Calif.). The DMEM-low glucose may be supplemented with 15% (v/v) fetal bovine serum (e.g. defined fetal bovine serum, Hyclone™, Logan Utah), antibiotics/antimycotics (such as penicillin (100 Units/milliliter), streptomycin (100 milligrams/milliliter), and amphotericin B (0.25 micrograms/milliliter), (Invitrogen®, Carlsbad, Calif.)), and 0.001% (v/v) 2-mercaptoethanol (Sigma®, St. Louis Mo.). In some cases, different growth media are used, or different supplementations are provided, and these are normally indicated as supplementations to Growth Medium. Also relating to the present invention, the term standard growth conditions, as used herein refers to culturing of cells at 37° C., in a standard atmosphere comprising 5% $CO_2$, where relative humidity is maintained at about 100%. While the foregoing conditions are useful for culturing, it is to be understood that such conditions are capable of being varied by the skilled artisan who will appreciate the options available in the art for culturing cells, for example, varying the temperature, $CO_2$, relative humidity, oxygen, growth medium, and the like.

Fibroblast cells used in the disclosed methods for obtaining conditioned media and/or regenerative factors can undergo at least 25, 30, 35, or 40 doublings prior to reaching a senescent state, in specific embodiments. Methods for deriving cells capable of doubling to reach $10^{14}$ cells or more are provided. In particular are those methods which derive cells that can double sufficiently to produce at least about $10^{14}$, $10^{15}$, $10^{16}$, or $10^{17}$ or more cells when seeded at from about $10^3$ to about $10^6$ cells/$cm^2$ in culture. In particular cases, these cell numbers are produced within 80, 70, or 60 days or less. In one embodiment, fibroblast cells used for the generation of conditioned media are isolated and expanded, and possess one or more markers selected from the group consisting of CD10, CD13, CD44, CD73, CD90, CD141, PDGFr-alpha, HLA-A, HLA-B, HLA-C, and a combination thereof. In some embodiments, the fibroblast cells do not produce one or more of CD31, CD34, CD45, CD117, CD141, HLA-DR, HLA-DP, or HLA-DQ.

In some cases, fibroblast cells are obtained from a biopsy, and the donor providing the biopsy may be either the individual to be treated (autologous), or the donor may be different from the individual to be treated (allogeneic). In cases wherein allogeneic fibroblast cells are utilized for an individual, the fibroblast cells may come from one or a plurality of donors.

The fibroblasts may be obtained from a source selected from the group consisting of dermal fibroblasts; placental fibroblasts; adipose fibroblasts; bone marrow fibroblasts; foreskin fibroblasts; umbilical cord fibroblasts; hair follicle derived fibroblasts; nail derived fibroblasts; endometrial derived fibroblasts; keloid derived fibroblasts; and a combination thereof.

In some embodiments, components obtained from culture of fibroblasts include one or more regenerative factors. Regenerative factors produced from fibroblasts cultured with an opioid receptor antagonist and a TLR agonist include, for example, epidermal growth factor (EGF), vascular endothelial growth factor (VEGF), fibroblast growth factor (FGF)-1, FGF-2, FGF-5, FGF-15, insulin like growth factor (IGF), placental growth factor, and hepatocyte growth factor (HGF). Regenerative factors may be isolated from cell culture media prior to use in the disclosed methods (e.g., stimulation of disc regeneration or repair). Alternatively, cell culture media may be used without isolating regenerative factors.

In some embodiments, components obtained from culture of fibroblasts include exosomes. Fibroblasts may produce exosomes comprising one or more regenerative factors (e.g., growth factors), which may be used in the disclosed methods (e.g., promotion of disc regeneration). Exosomes may be isolated from fibroblasts cultured with one or more opioid receptor antagonists and one or more TLR agonists, thereby obtaining one or more regenerative factors. Exosomes may be purified and concentrated from fibroblast cell culture media. In some embodiments, exosomes obtained from fibroblasts are between 60 and 200 nanometers in size. In some embodiments, exosomes obtained from fibroblasts stimulated with one or more opioid receptor antagonists and one or more TLR agonists are capable of inducing production of anti-inflammatory mediators (e.g., IL-10, IL-20, TGF-beta, etc.) from dendritic cells. In some embodiments, exosomes obtained from fibroblasts stimulated with an opioid receptor antagonist and a TLR agonist are capable of binding to mesenchymal stem cells and, in at least some cases, capable inducing production of TGF-beta from mesenchymal stem cells.

Culture conditioned media obtained from fibroblasts may be concentrated by filtering and/or desalting means. In one embodiment, Amicon® filters, or substantially equivalent means, with specific molecular weight cut-offs are utilized. Said cut-offs may select for molecular weights higher than 1 kDa to 50 kDa.

The cell culture supernatant may alternatively be concentrated using means known in the art such as solid phase extraction using C18 cartridges (Mini-Spe-ed C18-14%, S.P.E. Limited, Concord ON). Said cartridges are prepared by washing with methanol followed by deionized-distilled water. Up to 100 ml of stem cell or progenitor cell supernatant may be passed through each of these specific cartridges before elution, although it is understood by one of skill in the art that larger cartridges may be used. After washing the cartridges material adsorbed is eluted with 3 ml methanol, evaporated under a stream of nitrogen, redissolved in a small volume of methanol, and stored at 4° C.

Before testing the eluate for activity in vitro, the methanol is evaporated under nitrogen and replaced by culture medium. The C18 cartridges are used to adsorb small hydrophobic molecules from the stem or progenitor cell culture supernatant, and allows for the elimination of salts and other polar contaminants. It may, however be desired to use other adsorption means in order to purify certain compounds from said fibroblast cell supernatant. Said fibroblast concentrated supernatant may be assessed directly for biological activities useful for the practice of this invention, or may be further purified. In one embodiment, said supernatant of fibroblast culture is assessed for ability to stimulate proteoglycan synthesis using an in vitro bioassay. The in vitro bioassay allows for quantification and knowledge of which molecular weight fraction of supernatant possesses biological activity. Bioassays for testing ability to stimulate proteoglycan synthesis are known in the art. Production of various proteoglycans can be assessed by analysis of protein content using techniques including mass spectrometry, column chromatography, immune based assays such as enzyme linked immunosorbent assay (ELISA), immunohistochemistry, and flow cytometry.

Further purification may be performed using, for example, gel filtration using a Bio-Gel P-2 column with a nominal exclusion limit of 1800 Da (Bio-Rad®, Richmond Calif.). Said column may be washed and pre-swelled in 20 mM Tris-HCl buffer, pH 7.2 (Sigma®) and degassed by gentle swirling under vacuum. Bio-Gel P-2 material be packed into a 1.5×54 cm glass column and equilibrated with 3 column volumes of the same buffer. Amniotic fluid stem cell supernatant concentrates extracted by C18 cartridge may be dissolved in 0.5 ml of 20 mM Tris buffer, pH 7.2 and run through the column. Fractions may be collected from the column and analyzed for biological activity. Other purification, fractionation, and identification means are known to one skilled in the art and include anionic exchange chromatography, gas chromatography, high performance liquid chromatography, nuclear magnetic resonance, and mass spectrometry.

III. Examples of Methods of Use

Embodiments of the disclosure include means of augmenting regeneration of discs, which have undergone one or more degenerative processes, through introduction of components from fibroblasts which have been stimulated by one or more opioid receptor antagonists (e.g., naltrexone) alone and/or together with one or more toll like receptor (TLR) agonists. Components from fibroblasts may include conditioned media from culture of fibroblasts with one or more opioid receptor antagonists and one or more TLR agonists. Conditioned media may be used as a source of regenerative factors. Conditioned media may be concentrated. Components from fibroblasts may be administered to an individual in need of disc regeneration or repair (e.g., an individual with degenerative disc disease). Components may be administered intradiscally or systemically. In some embodiments, microvesicles and/or exosomes from stimulated fibroblasts are used as a source of regenerative factors.

In some aspects, this disclosure relates to methods for treating or preventing pathological intervertebral disc disorders by delivering one or more components from (e.g., secreted by, released by, etc.) fibroblasts stimulated with one or more opioid receptor antagonists and one or more TLR agonists. Stimulated fibroblasts may generate one or more regenerative factors suitable for administration to a disc and capable of stimulating disc regeneration. In some embodiments, one or more of these regenerative factors, in some cases together in a medium, are provided to an individual in need thereof. Alternatively or in addition, stimulated fibroblasts capable of producing regenerative factors may be delivered to an individual directly.

Embodiments of the disclosure encompass particular conditioned media, including for therapeutic use. In specific embodiments, the conditioned media is useful for stimulation of disc regeneration or repair in an individual, including one suffering from disc degenerative disease or at risk for disc degenerative disease (an individual at risk is an individual over the age of about 40, 45, 50, 55, 60, 65, 70, 75, 80, and so forth; an individual that is or was an athlete; an individual with a vocation that requires physical activity; an individual with a spinal injury; or a combination thereof, for example). Thus, in particular embodiments, disc degeneration is prevented utilizing methods encompassed by the disclosure or the disc degeneration may be delayed in onset and/or reduced in severity.

Conditioned media may be generated by stimulation of fibroblast cells that may be any kind of fibroblast cells. Such stimulation includes, in some embodiments, treatment with an effective amount of one or more opioid receptor antagonists and one or more TLR agonists sufficient to stimulate production of regenerative factors (e.g., one or more growth factors) by the fibroblast cells. Fibroblast cells may be stimulated with any opioid receptor antagonist including, for example, naltrexone, 6B-naltrexol, nalmefene, naloxone, N-methylnaltrexone, alvimopan, diprenorphine, nalorphine, nalorphine dinicotinate, levallorphan, samidorphan, nalodeine, naloxegol, axelopran, bevenopran, methylsamidorphan, or naldemedine. In some embodiments, fibroblast cells are stimulated with naltrexone. Fibroblast cells may be stimulated with any TLR agonist including, for example, Pam3CSK4, LPS, CpG DNA, Poly (ic), flagellin, MALP-2, imiquimod, resmiquimod, zymosan, or a combination thereof. Conditioned media generated from stimulation of fibroblast cells may be obtained, in some cases concentration, and provided to an individual in need thereof.

In some embodiments, fibroblast conditioned media is utilized as part of a formulation with other therapeutic compounds where the formulation is administered intradiscally or systemically to an individual in order to induce proteoglycan production from the disc. Compounds can be vitamin A, vitamin C, vitamin D, vitamin E, vitamin K, folic acid, choline, vitamin B1, vitamin B2, vitamin B5, vitamin B6, vitamin B12, biotin, nicotinamide, betacarotene, coenzyme Q, selenium, superoxide dismutase, glutathione peroxide, uridine, creatine succinate, pyruvate, dihydroxyacetone), acetyl-L-carnitine, alpha-lipoic acid, cardiolipin, omega fatty acid, lithium carbonate, lithium citrate, calcium, or any combination thereof. In some aspects, the compounds are anti-inflammatory agents. In some aspects, the anti-inflammatory agents include one or more of Alclofenac; Alclometasone Dipropionate; Algestone Acetonide; Alpha Amylase; Alpha-lipoic acid; Alpha tocopherol; Amcinafal; Amcinafide; Amfenac Sodium; Amiprilose Hydrochloride; Anakinra; Anirolac; Anitrazafen; Apazone; Ascorbic Acid; Balsalazide Disodium; Bendazac; Benoxaprofen; Benzydamine Hydrochloride; Bromelains; Broperamole; Budesonide; Carprofen; Chlorogenic acid; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Ellagic acid; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Glutathione; Halcinonide; Halobetasol Propionate; Halopredone Acetate; Hesperedin; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lomoxicam; Loteprednol Etabonate; Lycopene; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Oleuropein; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Pycnogenol; Polyphenols; Prednazate; Prifelone; Prodolic Acid; Proquazone; Proxazole; Proxazole Citrate; Quercetin; Reseveratrol; Rimexolone; Romazarit; Rosmarinic acid; Rutin; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrahydrocurcumin; Tetrydamine; Tiopinac; Tixocortol Pivalate; Tolmetin; Tolmetin Sodium; Triclonide; Triflumidate; Zidometacin; Zomepirac Sodium. In some aspects the compounds are bioactive compounds including but not limited to growth factors, cytokines, antibodies, antibody fragments, and/or organic molecules of a mass of less than 5000 daltons. The compounds may be administered concurrently with a composition of the current disclosure. Alternatively, the compounds may be administered before and/or after the composition is administered to a subject.

IV. Obtaining Fibroblast Regenerative Cells

Embodiments of the disclosure include methods for obtaining or isolating regenerative fibroblast cells. Obtaining regenerative fibroblast cells may comprise enriching a population of regenerative fibroblast cells from a tissue having regenerative activity. In some embodiments, regenerative fibroblast cells are obtained from a tissue having regenerative activity by enriching for cells that are about 6-12 μm in size, which express at least one of Oct-4, Nanog, Sox-2, KLF4, c-Myc, Rex-1, GDF-3, LIF receptor, CD105, CD117, CD344 and Stella, and which do not express at least one of MHC class I, MHC class II, CD45, CD13, CD49c, CD66b, CD73, CD105, or CD90 cell surface proteins. In some embodiments, cell types such as granulocytes, T-cells, B-cells, NK-cell, red blood cells, or any combination thereof, are separated from fibroblast regenerative cells. In some aspects, separating the cell types is done by cell depletion. In some embodiments, fibroblast regenerative cells are enriched by flow cytometry.

Further embodiments of the current disclosure relate to methods of identifying a fibroblast regenerative cell. In some embodiments, a vector comprising a fibroblast cell-specific promoter coupled to at least one selectable marker gene is introduced into a cell. The selectable marker gene may be expressed from the cell-specific promoter in the cell and detected, thereby identifying the fibroblast regenerative cell. In some embodiments, the fibroblast regenerative cell does not express at least one of MHC class I, MHC class II, CD44, CD45, CD13, CD34, CD49c, CD66b, CD73, CD105, and CD90 cell surface proteins. In some embodiments, the fibroblast regenerative cell expresses at least one of Oct-4, Nanog, Sox-2, Rex-1, GDF-3, Stella, FoxD3, or Polycomb embryonic transcription factors. In some embodiments, the fibroblast regenerative cell does not express CD13, CD44, CD90, or a combination thereof.

In some embodiments, the vector is a retroviral vector. In some embodiments, the selectable marker gene encodes a fluorescent protein (e.g., Green Fluorescent Protein (GFP)). In some embodiments, the vector comprises two selectable marker genes, where the two selectable marker genes comprise a fluorescent protein, a protein sensitive to drug selection, a cell surface protein or any combination thereof. In some embodiments, the fibroblast cell-specific promoter is an Oct-4 promoter, a Nanog promoter, a Sox-2 promoter, a Rex-1 promoter, a GDF-3 promoter, aStella promoter, a FoxD3 promoter, a Polycomb Repressor Complex 2 promoter, or aCTCF promoter. In some embodiments, the fibroblast cell-specific promoter is flanked by loxP sites.

In some embodiments, the fibroblast regenerative cell is capable of differentiating into mesoderm, ectoderm, and/or endoderm. In some aspects, the fibroblast regenerative cell further comprises a rhodamine 123 efflux activity. In further aspects, the fibroblast regenerative cell has enhanced expression of GDF-11 as compared to a control. In some embodiments, the disclosed methods comprise transfecting a fibroblast regenerative cell with a transcription factor capable of enhancing the regenerative activity of the fibroblast regenerative cell. In some embodiments, the fibroblast regenerative cell is transfected with an OCT-4 transcription factor. In some embodiments, regenerative fibroblast cells are fused with cells having a pluripotent ability, thereby generating fibroblasts with enhanced regenerative activity.

In some embodiments, the disclosed methods comprise isolating a fibroblast regenerative cell from a mammal. In some embodiments, the fibroblast regenerative cell is derived from bodily fluid of the mammal. In some embodiments, the fibroblast regenerative cell is derived from tissue of the mammal. In some embodiments, the mammal is a human. In some embodiments, fibroblasts are enriched by contacting cells with a detectable compound that enters the cells, the compound being selectively detectable in proliferating and non-proliferating cells, and proliferating cells enriched based on detection of the compound. In some embodiments, the detectable compound is carboxyfluorescein diacetate, succinimidyl ester, or Aldefluor™. In some cases, fibroblasts expressing one or more markers may be selected. In some embodiments, fibroblast cells expressing CD105 and/or CD117 are selected. Fibroblast cells expressing CD105 and/or CD117 may be transfected with a NANOG gene.

Cells expressing cell surface markers or MHC proteins may be separated or depleted from a population of fibroblast cells, thereby isolating a population of stem cells. In some embodiments, the cell to be depleted express MHC class I, CD66b, glycophorin a, or glycophorin b. Cells may be transfected with a stem cell-specific promoter operably linked to a reporter or selection gene. A stem cell-specific promoter may be, for example, an Oct-4, Nanog, Sox-9, GDF3, Rex-1, or Sox-2 promoter.

V. Kits of the Disclosure

Any of the cellular and/or non-cellular compositions described herein or similar thereto may be comprised in a kit. In a non-limiting example, one or more reagents for use in methods for preparing fibroblasts may be comprised in a kit. Such reagents may include cells, vectors, one or more growth factors, vector(s) one or more costimulatory factors, media, enzymes, buffers, nucleotides, salts, primers, compounds, and so forth. The kit components are provided in suitable container means.

Some components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present disclosure also will typically include a means for containing the components in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly useful. In some cases, the container means may itself be a syringe, pipette, and/or other such like apparatus, or may be a substrate with multiple compartments for a desired reaction.

Some components of the kit may be provided as dried powder(s). When reagents and/or components are provided as a dry powder, the powder can be reconstituted by the addition of a suitable solvent. It is envisioned that the solvent may also be provided in another container means. The kits may also comprise a second container means for containing a sterile acceptable buffer and/or other diluent.

In specific embodiments, reagents and materials include primers for amplifying desired sequences, nucleotides, suitable buffers or buffer reagents, salt, and so forth, and in some cases the reagents include apparatus or reagents for isolation of a particular desired cell(s).

In particular embodiments, there are one or more apparatuses in the kit suitable for extracting one or more samples from an individual. The apparatus may be a syringe, fine needles, scalpel, and so forth.

EXAMPLES

The following examples are included to demonstrate particular embodiments of the invention. It should be appreciated by those of skill in the art that the techniques disclosed in the examples that follow represent techniques discovered by the inventors to function well in the practice of the methods of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Stimulation of Regenerative Growth Factor Production in Fibroblasts by Naltrexone Combined with Toll Like Receptor Agonists The present example characterizes the use of naltrexone and a TLR agonist to stimulate EGF production in foreskin fibroblasts as an example of a type of fibroblasts.

Neonatal foreskin fibroblasts were obtained from ATCC and cultured in typical DMEM culture media containing 10% fetal calf serum and antibiotics. After 3 days of culture, fibroblasts where plated in 12 well plates and cultured at 50% confluent conditions. Addition of naltrexone (Sigma Aldrich®) and the indicated TLR agonists was performed for 12 hours of culture. Pam3CSK4 was added at a total concentration of 1 ug/ml. LPS was added at 0.5 ug/ml. CpG was added at 0.2 ug/ml. Concentration of EGF was assessed using ELISA (R&D Systems). Results are shown in FIG. 1.

What is claimed is:

1. A method of promoting disc regeneration in an individual, the method comprising providing to the individual an effective amount of fibroblast cells previously cultured with one or more opioid receptor antagonists and one or more toll-like receptor (TLR) agonists.

2. The method of claim 1, wherein the opioid receptor antagonist is 6B-naltrexol, nalmefene, naloxone, N-methylnaltrexone, alvimopan, diprenorphine, nalorphine, nalorphine dinicotinate, levallorphan, samidorphan, nalodeine, naloxegol, axelopran, bevenopran, methylsamidorphan, naldemedine, or a combination thereof.

3. The method of claim 1, wherein the TLR agonist is Pam3CSK4, LPS, CpG DNA, Poly (ic), flagellin, MALP-2, imiquimod, resmiquimod, zymosan, or a combination thereof.

4. The method of claim 1, wherein:

(a) the fibroblast cells were cultured with the opioid receptor antagonist and the TLR agonist in a proliferative state;

(b) the fibroblast cells express a marker selected from the group consisting of Oct-4, Nanog, Sox-2, KLF4, c-Myc, Rex-1, GDF-3, LIF receptor, CD105, CD117, CD344, Stella, CD10, CD13, CD44, CD73, CD90, CD141, PDGFr-alpha, HLA-A, HLA-B, HLA-C, and a combination thereof; and/or (c) the fibroblast cells do not express a marker selected from the group consisting of MHC class I, MHC class II, CD45, CD13, CD49c, CD66b, CD73, CD105, CD90, CD31, CD34, CD45, CD117, CD141, HLA-DR, HLA-DP, HLA-DQ, and a combination thereof.

5. The method of claim 4, wherein the fibroblast cells were cultured with the opioid receptor antagonist and the TLR agonist in a proliferative state.

6. The method of claim 4, wherein the fibroblast cells express a marker selected from the group consisting of Oct-4, Nanog, Sox-2, KLF4, c-Myc, Rex-1, GDF-3, LIF receptor, CD105, CD117, CD344, Stella, CD10, CD13, CD44, CD73, CD90, CD141, PDGFr-alpha, HLA-A, HLA-B, HLA-C, and a combination thereof.

7. The method of claim 4, wherein the fibroblast cells do not express a marker selected from the group consisting of MHC class I, MHC class II, CD45, CD13, CD49c, CD66b, CD73, CD105, CD90, CD31, CD34, CD45, CD117, CD141, HLA-DR, HLA-DP, HLA-DQ, and a combination thereof.

8. The method of claim 1, wherein the fibroblast cells are administered to the individual intradiscally or systemically.

* * * * *